United States Patent [19]

Wolf et al.

[11] 4,326,073

[45] Apr. 20, 1982

[54] PRODUCTION OF ANHYDROUS OR SUBSTANTIALLY ANHYDROUS FORMIC ACID

[75] Inventors: Dieter Wolf, Gruenstadt; Rudolf Schmidt, Frankenthal; Ulrich Block, Ludwigshafen; Hartmut Schoenmakers, Heidelberg; Kaspar Bott, Wachenheim; Gerd Kaibel, Lampertheim, all of Fed. Rep. of Germany

[73] Assignee: BASF Aktiengesellschaft, Ludwigshafen, Fed. Rep. of Germany

[21] Appl. No.: 131,501

[22] Filed: Mar. 18, 1980

[30] Foreign Application Priority Data

Apr. 11, 1979 [DE] Fed. Rep. of Germany ....... 2914671

[51] Int. Cl.$^3$ .............................................. C07C 51/09
[52] U.S. Cl. ....................................... 562/609; 203/84
[58] Field of Search .......................... 562/609; 203/84

[56] References Cited

U.S. PATENT DOCUMENTS

| | | | |
|---|---|---|---|
| 3,983,010 | 9/1976 | Rauch et al. | 562/609 |
| 4,076,594 | 2/1978 | Buelow et al. | 562/609 |
| 4,143,066 | 3/1979 | Kalcevic | 562/513 |
| 4,217,460 | 8/1980 | Hohenschutz et al. | 562/609 |
| 4,218,568 | 8/1980 | Hohenschutz | 562/609 |
| 4,262,140 | 4/1981 | Bott et al. | 562/609 |

*Primary Examiner*—Joseph E. Evans
*Assistant Examiner*—Vera C. Clarke
*Attorney, Agent, or Firm*—John H. Shurtleff

[57] ABSTRACT

Anhydrous or substantially anhydrous formic acid is obtained by hydrolysis of methyl formate, in a process wherein (a) methyl formate is hydrolyzed,
(b) the methanol and excess methyl formate are distilled from the hydrolysis mixture obtained,
(c) the bottom product of distillation (b), consisting of formic acid and water, is extracted, in a liquid-liquid extraction, with an extractant which in the main takes up the formic acid,
(d) the resulting extract phase, consisting of formic acid, the extractant and a part of the water, is subjected to distillation,
(e) the top product obtained from this distillation and consisting of all or part of the water introduced into the distillation, and part of the formic acid, is recycled, as vapor, into the lower part of the distillation column of stage (b),
(f) the bottom product of distillation stage (d), consisting of the extractant, with or without part of the water, and the greater part of the formic acid, is separated by distillation into anhydrous or substantially anhydrous formic acid and the extractant, and
(g) the extractant leaving stage (f) is recycled to the process.

12 Claims, 2 Drawing Figures

Figure 1:
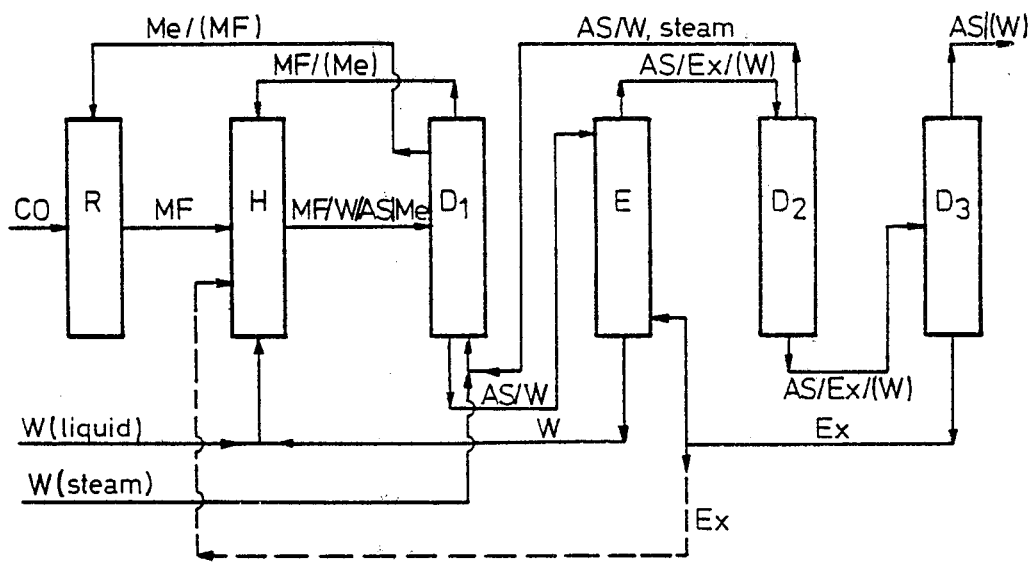

Me = methanol
MF = methyl formate
AS = formic acid
W = water
Ex = extractant
( ) = minor amounts for explanation see figure 1

PRODUCTION OF ANHYDROUS OR SUBSTANTIALLY ANHYDROUS FORMIC ACID

The present invention relates to a novel process for producing anhydrous or substantially anhydrous formic acid from aqueous solutions obtained from the hydrolysis of methyl formate.

Ullmanns Encyklopädie der technischen Chemie, 4th edition, volume 7, page 365, discloses that formic acid may be prepared by acidolysis of formamide with sulfuric acid. This process, which is operated industrially, however has the disadvantage that stoichiometric amounts of ammonium sulfate are necessarily produced at the same time.

In spite of this disadvantage, the hydrolysis of methyl formate $$HCOOCH_3 + H_2O \rightleftharpoons HCOOH + CH_3OH$$

which has also been disclosed (Ullmann, loc. cit., page 366) and which at first sight appears substantially more advantageous, has hitherto not found industrial acceptance, in the main because of the high rate of reesterification resulting from the catalytic action of formic acid, since the latter is a strong acid. Accordingly, the hydrolysis equilibrium is unfavorable, all four components being present in substantial amounts.

Shifting the equilibrium by distillative removal of the desired product is not feasible, because methyl formate (boiling point 32° C.) is substantially lower-boiling than methanol (boiling point 65° C.) and formic acid (boiling point 101° C.).

Previous attempts to remove formic acid from the equilibrium mixture by means of an extractant have also not proved satisfactory.

Thus, German Laid-Open Application DOS No. 2,744,313 discloses that the hydrolysis may be carried out in the presence of an organic base, in which case an adduct of formic acid and the base is formed, from which adduct the other reactants can easily be removed by distillation. However, disadvantages of this process are not only that the distillation expense involved in total is too great, but also that the cleavage of the adduct requires relatively severe distillation conditions, under which the formic acid and the base begin to decompose. Consequently, it is necessary to redistil the formic acid. Accordingly, pure formic acid cannot be prepared economically from methyl formate by this process.

According to German Laid-Open Application DOS No. 2,545,658, aqueous formic acid, such as is obtained after distillative removal of methyl formate and methanol from the hydrolysis mixture, is subjected to a liquid-liquid extraction with N-di-n-butylformamide or similar carboxylic acid amides. However, by itself this process does not amount to a solution of the problem of the economical isolation of formic acid on an industrial scale.

According to the process of the earlier German Patent Application No. P 28 59 991, the hydrolysis of methyl formate and the dehydration of formic acid are carried out in one and the same reaction column.

Not the least of the reasons why the energy balance of all conventional processes is unsatisfactory is because all the water, or at least a large part thereof, must constantly be recycled, involving evaporation and condensation. Hence, because of the high heat of vaporization of water, a particularly large amount of energy is lost.

For this reason, attempts have constantly been made to minimize the water content, ie. to use not substantially more than the stoichiometric amount required for hydrolysis. This eliminated the possibility of shifting the hydrolysis equilibrium in favor of formic acid by using an excess of water.

It is an object of the present invention to isolate anhydrous or substantially anhydrous formic acid more economically from methyl formate hydrolysis mixtures.

We have found that this object is achieved and that anhydrous or substantially anhydrous formic acid is obtained by hydrolysis of methyl formate if (a) methyl formate is hydrolyzed, (b) the methanol and excess methyl formate are distilled from the hydrolysis mixture obtained, (c) the bottom product of distillation (b), consisting of formic acid and water, is extracted, in a liquid-liquid extraction, with an extractant which in the main takes up the formic acid, (d) the resulting extract phase, consisting of formic acid, the extractant and a part of the water, is subjected to distillation, (e) the top product obtained from this distillation and consisting of all or part of the water introduced into the distillation, and part of the formic acid, is recycled, as vapor, into the lower part of the distillation column of stage (b), (f) the bottom product of distillation stage (d), consisting of the extractant, with or without part of the water, and the greater part of the formic acid, is separated by distillation into anhydrous or substantially anhydrous formic acid and the extractant, and (g) the extractant leaving stage (f) is recycled to the process.

Further, we have found that it is particularly advantageous, in this process, if (h) the distillation steps (b) and (d) are carried out in a single column which performs the functions of the columns referred to in these steps, and/or (i) the water required for hydrolysis is introduced as water vapor into the lower part of the column of step (b) and/or (k) methyl formate and water are employed in a molar ratio of from 1:2 to 1:10 in the hydrolysis (a) and/or (l) the extractant used in a carboxylic acid amide of the general formula I

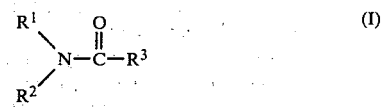

where $R^1$ and $R^2$ are alkyl, cycloalkyl, aryl or aralkyl or conjointly are 1,4- or 1,5-alkylene, each of 1 to 8 carbon atoms, with the proviso that the sum of the carbon atoms of $R^1$ and $R^2$ is from 7 to 14, and that only one of the radicals is aryl, and where $R^3$ is preferably hydrogen, or $C_1$-$C_4$-alkyl, and/or (m) if an extractant (I) is used, the hydrolysis (a) is carried out in the presence of the extractant.

Figure 2:
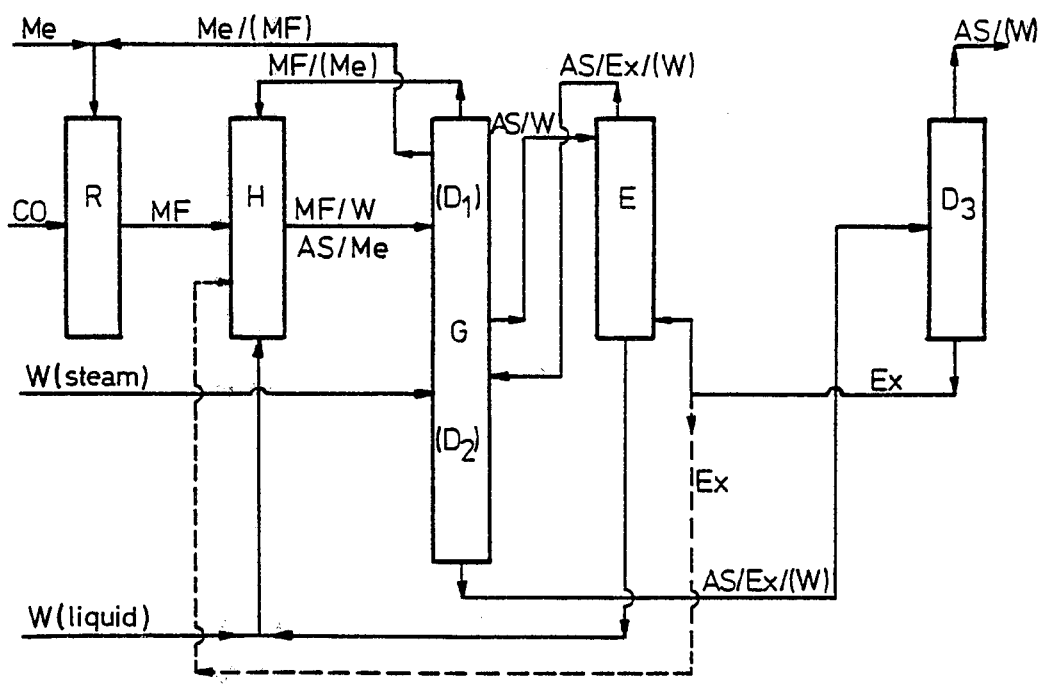

The process according to the invention is illustrated in FIGS. 1 and 2, specifically to illustrate the advantages achievable by the combination of steps, in each case as part of the total synthesis of formic acid from carbon monoxide and water in accordance with the following reactions:

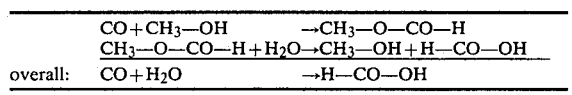

overall: $CO + H_2O \rightarrow H\text{—}CO\text{—}OH$

The fact that there is some consumption of the auxiliary material such as methanol or the extractant is self-evident and does not require more detailed explanation.

FIG. 1 shows the process, carried out in the apparatus H, $D_1$, E, $D_2$ and $D_3$, in the general form according to process characteristics (a) to (g).

The mixture of methyl formate (MF), water (W), formic acid (AS) and methanol (Me) leaving the hydrolysis reactor H first passes into the distillation column $D_1$, in which methyl formate and methanol are distilled from the aqueous formic acid in accordance with process step (b). As part of the total synthesis, this step is advantageously carried out in such a way that the methyl formate, which does not have to be completely free from methanol, is taken off at the top and recycled to the hydrolysis reactor H, and the methanol, which can still contain some methyl formate, is taken off as a higher-boiling side stream and recycled to the synthesis reactor R.

The bottom product of $D_1$, consisting of formic acid and water, passes into the liquid-liquid extraction column E, where it is substantially freed from water, in accordance with process step (c), by counter-current treatment with the extractant (Ex). In most cases, water and formic acid are heavier than the extractant and than the extract phase consisting principally of the extractant, formic acid and water, and this determines the inlet and outlet points of E. If the converse applies, the inlet and outlet points have to be interchanged accordingly. The water, which normally leaves E at the bottom, is advantageouly recycled to H, whilst the extract phase, which always still contains water, passes into the distillation column $D_2$.

The top product of this distillation (d), which in the main consists of water and small proportions of formic acid, is recycled as vapor to $D_1$, in accordance with process step (e), where it provides part or all of the energy required in $D_1$. The bottom product from $D_2$, consisting of formic acid and the extractant, is separated in $D_3$ into its components, in accordance with process step (f), after which the extractant is recycled to E in accordance with process step (g). If it is desired to use the special embodiment (m), part of the extractant is recycled to the hydrolysis reactor H, as illustrated by the line shown broken. In that case, the product stream from H via $D_1$ to E additionally contains the extractant.

If the separating efficiency in $D_2$ is reduced, the bottom product of $D_2$ is an aqueous mixture which in $D_3$ gives, instead of anhydrous formic acid, a formic acid of corresponding water content; such a product is adequate for many purposes.

The water required for the hydrolysis may be introduced as liquid. If, however, industrial steam is in any case available, the water is preferably introduced as steam, because this provides part of the energy requirement. For example, the steam can be taken up into the stream $D_2$-$D_1$ and be led into the lower part of $D_1$.

FIG. 2 illustrates the spatial combination of the process steps (b) and (d), carried out in distillation columns $D_1$ and $D_2$, in a single combined column G, in accordance with the preferred embodiment (h). As may be seen, the difference from the general flow chart is simply that the line "AS/W, steam" from $D_2$ to $D_1$ is omitted, since $D_1$ and $D_2$ are short-circuited. More detailed explanation of FIG. 2 is therefore superfluous.

Specifically, process steps (a) to (m), and their apparatus, advantageously conform to the following embodiments.

Process step (a)

The hydrolysis (a) is in general carried out in a conventional manner at 80°–150° C. The special embodiments (k) and (m) will be discussed below.

Process step (b)

The distillation of the hydrolysis mixture can in principle be carried out under any desired pressure (say from 0.5 to 2 bar), but in general it is advisable to operate under atmospheric pressure. In that case, the column bottom is at about 110° C. and the column top at about 30°–40° C. The hydrolysis mixture is advantageously added at from 80° to 150° C., and the methanol is taken off as liquid at from 55° to 65° C. Satisfactory separation of the mixture into methyl formate and methanol on the one hand and aqueous formic acid on the other hand is feasible with as few as 25 theoretical plates, whilst more than 60 theoretical plates offers no further significant advantages. Preferably, from 35 to 45 theoretical plates are employed. The construction of column $D_1$ can be of any desired type, but perforated tray columns or packed columns are particularly advantageous, because they can be produced relatively simply from corrosion-resistant materials, so that they are cheaper than columns of other type of construction.

The methanol and the methyl formate are advantageously recycled into the synthesis reactor R or the hydrolysis reactor H, but this is not an essential feature of the process according to the invention. Since small amounts of methyl formate do not interefere with the synthesis, and small amounts of methanol do not interfere with the hydrolysis, the distillative separation of methyl formate from methanol need not be complete. In general, it suffices if each material is 90% by weight pure.

Process step (c)

The liquid-liquid extraction of the formic acid from its aqueous solution by means of an extractant is preferably carried out under atmospheric pressure at from 60° to 120° C., especially from 70° to 90° C., in counter-current, by a conventional technique. Depending on the nature of the extractant, the separating equipment as a rule requires to have from 1 to 12 theoretical separation stages; where there is only one stage, the column simply becomes a separator. In most cases, satisfactory results are achieved with from 4 to 6 theoretical separation stages. In principle, the process is not dependent on the type of construction of the separation apparatus, ie. perforated tray columns or packed columns, with or without pulsation, may be used, as can apparatus with rotating inserts, or mixer-settler batteries.

The nature of the extractant is not a critical feature of the invention; rather all liquids which dissolve formic acid and which are immiscible or only slightly miscible with water may be used. However, these preconditions per se are in most cases not a sufficient criterion for industrial purposes. If, for example, an extractant which has only a slight affinity for polar hydrophilic compounds, such as benzene or a chlorohydrocarbon, is used, the extract phase, it is true, contains little water and a relatively large amount of formic acid, but in absolute terms contains only little formic acid. In this case it would therefore be necessary, in order to achieve adequate production capacities, to recycle disproportionately large amounts of the extractant, entailing expensive apparatus and high energy consumption.

If, on the other hand, the affinity of the extractant for formic acid is very high, a large amount of water in most cases also passes into the extract phase, because of the high affinity of water for formic acid. This is also a disadvantage, though not so important in the process of the present invention. The economical compromise between the disadvantages of a selective extractant, which however has a low capacity, and a less selective extractant, which however has a higher capacity, therefore tends to be nearer the latter alternative.

The mode of action of the extractant may be a purely physical solution process or a chemical absorption, with formation of thermally easily decomposable saline compounds or hydrogen bridge adducts. If the latter is the case, the extractant is preferably employed in about equilmolar amount, or slight excess, relative to formic acid, ie. in a molar ratio of Ex:FA of from 1:1 to 3:1. In the case of a (physical) solution process, the volume ratio Ex:FA is in general from 2:1 to 5:1. For intermediate embodiments between solution extraction and chemical absorption, corresponding average values between the two ranges mentioned apply.

Extractants which have proved particularly suitable are the carboxylic acid amides, exerting a certain amount of chemical affinity, of the general formula I

where $R^1$ and $R^2$ are alkyl, cycloalkyl, aryl or arakyl or conjointly are 1,4- or 1,5-alkylene, each of 1 to 8 carbon atoms, with the proviso that the sum of the carbon atoms of $R^1$ and $R^2$ is from 7 to 14, and that only one of the radicals is aryl, and where $R^3$ is preferably hydrogen, or $C_1$-$C_4$-alkyl.

Such extractants are, in particular, N-di-n-butylformamide, as well as N-di-n-butylacetamide, N-methyl-N-2-heptylformamide, N-n-butyl-N-2-ethylhexylformamide, N-n-butyl-N-cyclohexylformamide, N-ethylformanilide and mixtures of these compounds. The formamides are in general preferred, because in the case of the amides of higher acids there is a possibility of transamidation, which can lead to liberation of these acids by the formic acid.

Further suitable extractants include diisopropyl ether, methyl isobutyl ketone, ethyl acetate, tributyl phosphate and butanediol formate.

The raffinate phase obtaned in every case is almost exclusively water, with some formic acid and small amounts of the extractant. The concomitant materials however do not interfere, since they are returned to the extraction stage in the course of the process cycle.

The extract phase consists in the main of virtually all the formic acid, virtually all the extractant, and from about 30 to 60% by weight, based on formic acid, of water.

Process step (d)

The extract phase from E is separated by distillation, in column $D_2$, into a liquid phase which consists of the formic acid, the extractant and—where it is intended to obtain aqueous formic acid—some water, and a vapor phase consisting of water and small amounts of formic acid. Since an extractant is present which takes into the liquid phase the formic acid which in part evaporates alongside the evaporation of water, process step (d) can also be regarded as an extractive distillation.

The bottom temperature for this distillation is preferably from 140° to 180° C. A complete separation effect, ie. a separation where no water enters the bottom product, is achieved with 5 or more theoretical plates. However, if 90% strength by weight aqueous formic acid is to be obtained, 5 theoretical plates are still necessary, and it is only at even lower concentrations that from 4 to 3 plates suffice. As in the case of column $D_1$, the type of construction of column $D_2$ is immaterial, so that the same remarks apply as to column $D_1$.

Process step (e)

The recycling of the formic acid/water mixture, in vapor form, from $D_2$ to $D_1$ is a particularly important feature of the invention. It means, in comparison with conventional processes, that regardless of the total amount of water, it is only necessary to vaporize the amount of water which passes into the extract phase during the extraction, and that the heat of vaporization can be re-utilized directly in $D_1$. Since this energy would in any case have to be expended, the extractive distillation in $D_2$ takes place substantially energy-free.

Compared to conventional procedures, the energy saving is at least 5 Gigajoule per tonne of pure formic acid.

Process steps (f) and (g)

These process steps correspond to the conventional technique and thus do not contribute to the essentials of the invention. They are mentioned separately merely to ensure that the invention provides a complete teaching. It should merely be noted that the column $D_3$ is advantageously operated under reduced pressure and at a correspondingly low top temperature, namely at from about 50 to 300 mbar and from 30° to 60° C., so that the formic acid should not decompose.

Process characteristic (h)

This embodiment of the novel process corresponds to steps (b) and (d), if columns $D_1$ and $D_2$ are arranged one above the other to form a combined column G, and are thus short-circuited, with omission of the line $D_2$-$D_1$. The advantages of this particularly elegant embodiment of the process, in which, in other respects, the details concerning process steps (b) and (d) still apply, are self-evident and further explanations are therefore superfluous.

Process characteristic (i)

This is again an embodiment of the invention which is intended to introduce heat energy in the form of steam into the process simultaneously with the water which is required in any case for the hydrolysis, provided industrial steam is available. If it is not available, the fresh water can also be introduced as liquid at virtually any desired point of the hydrolysis reactor.

Process characteristic (k)

This embodiment is particularly inventive, since it is now economically possible, in combination with the other characteristics of the process, to start from a hydrolysis mixture which has in turn been prepared from methyl formate and a molar excess of water. This shifts the equilibrium in favor of formic acid, so that the expense of distilling unconverted methyl formate is reduced and the capacity for production of formic acid is increased. Larger apparatus may be required as a result of the larger amount of water, but the energy consumption is virtually not increased, since the additional water remains in the liquid circulation system and does not have to be vaporized.

Process characteristics (l)

This concerns the fact that extractants (I), especially di-n-butylformamide, are particularly suitable. Further details are given under (c).

Process characteristic (m)

We have found that the equilibrium in hydrolysis step (a) can be shifted in favor of formic acid if the hydrolysis is carried out in the presence of one of the extractants (I), especially N-di-n-butylformamide. Preferably, from 0.5 to 2 moles of (I) are employed per mole of methyl formate. In that case, the preferred amount of water is also from 0.5 to 2 moles per mole of methyl formate. Accordingly, the amount of water in the water circulation system can be substantially reduced with this procedure. Consequently, the efficiency of the extraction is increased, so that, in this case specifically, as little as one separating stage suffices, ie. a simple separator may be used. As, consequently, less extractant is required for the extraction, procedure (h) is particularly advisable in this case, since there is only as much extractant as is required for the extraction passes from $D_3$ to $E_1$. By contrast, in the basic procedure which includes the individual steps (b) and (d) instead of the combined step (h), the total amount of extractant passes into E, which is why E must be made correspondingly larger. From an energy point of view, however, this does not mean any disadvantage.

Apart from slight losses of raw materials and auxiliary materials, inherent in the process technology, only water and carbon monoxide are required as starting materials for the total synthesis of formic acid. By slightly modifying the process conditions, all conventional commercial grades of formic acid, ranging from about 75% strength by weight to virtually 100% strength acid, can be produced in one and the same installation.

EXAMPLE 1

This Example was carried out in an experimental apparatus as shown in FIG. 2, ie. in accordance with the preferred embodiment, including characteristic (h).

Per hour, 1,734 g of a hydrolysis mixture, obtained at 120° C., of 16.8% by weight of formic acid, 16.4% by weight of methyl formate, 12.3% by weight of methanol and 54.2% by weight of water were fed, at 120° C., into a combined column G of 5 cm internal diameter and 5 m height, with 80 bubble-cap trays, at the level of the 35th tray (counted from the bottom). The mixture mentioned corresponds to an original methyl formate/water ratio, for the hydrolysis, of 1:5.3.

In steady state operation, 167 g of methanol and 25 g of methyl formate were taken off per hour, as liquid at 60° C., at the level of the 70th tray, whilst 313 g of methyl formate and 17 g of methanol per hour were taken off at 34° C., at the column top. The methyl formate fraction was passed into the hydrolysis reactor H and the methanol fraction into the synthesis reactor R. Per hour, 1,528 g of a mixture of 268 g of formic acid, 28 g of N-di-n-butylformamide and 1,232 g of water were taken off at 104° C., at the level of the 21st tray, and passed into the top of a pulsation extraction column E, of 3 m height and 3 cm internal diameter, packed with 3 mm glass rings. This column had 6 theoretical plates. 1,287 g of N-di-n-butylformamide per hour, ie. 1.54 moles per mole of formic acid, were introduced in counter-current.

The extract phase obtained per hour was a mixture of 1,306 g of the extractant, 266 g of formic acid and 180 g of water, and this, together with 106 g of fresh water, was passed into column G at the level of the 20th tray.

The raffinate phase obtained from E, and consisting of 1,052 g of water, 6 g of formic acid and 5 g of extractant per hour, was recycled to the hydrolysis reactor H.

Per hour, a mixture of 248 g of formic acid, 10 g of water and 1,283 g of extractant was taken from the bottom of column G at 170° C. and charged onto the 10th tray of a bubble-cap tray column $D_3$, having a height of 2.5 m and internal diameter of 5 cm, and possessing 30 trays.

Distillation under 93 mbar pressure at the top, with a reflux ratio of 1.5, gave 255 g per hour of 96% strength by weight formic acid. The extractant, still containing small amounts of water, was recycled into the extraction column.

EXAMPLE 2

This procedure in principle resembled that of Example 1, except for the important difference that the hydrolysis of the methyl formate was carried out at 140° C. in the presence of N-di-n-butylformamide, as a result of which the amounts of the components in the product streams required to achieve the same yield of formic acid were different. The amount of hydrolysis mixture was now 2,017 g per hour, the composition being 12.6% by weight of methyl formate, 9.3% by weight of methanol, 15.3% by weight of water and 43.5% by weight of extractant.

Only 367 g per hour of the extractant were required for the extraction in the present case. As in Example 1, 245 g per hour of 96% strength by weight formic acid were obtained.

We claim:

1. In a process for obtaining anhydrous or substantially anhydrous formic acid by hydrolysis of methyl formate, the improvement which comprises:
    (a) hydrolyzing methyl formate;
    (b) in a first stage distillation column, distilling methanol and excess methyl formate from the hydrolysis mixture obtained in step (a);
    (c) extracting the bottom product of the first distillation stage (b), consisting essentially of formic acid and water, by means of a liquid-liquid extraction with an extractant which in the main takes up the formic acid;
    (d) in a second stage distillation column, distilling the extract phase, consisting essentially of formic acid, the extractant and a part of the water;

(e) recycling, as vapor, into the lower part of the distillation column of stage (b), the top product obtained from the second distillation stage (d) and consisting essentially of
  (1) all or part of the water introduced into said second stage (d), and
  (2) part of the formic acid;
(f) separating, by distillation in a third stage distillation column, the bottom product of distillation stage (d) consisting essentially of
  (1) the extractant with or without part of the water, and
  (2) the greater part of the formic acid into anhydrous or substantially anhydrous formic acid and the extractant; and
(g) recycling to the process the extractant leaving the third distillation stage (f).

2. A process as claimed in claim 1, wherein the distillation steps (b) and (d) are carried out in a single column which performs the functions of the columns of these steps.

3. A process as claimed in claim 1, wherein the water required for the hydrolysis is introduced as steam into the lower part of the column of step (b).

4. A process as claimed in claim 2, wherein the water required for the hydrolysis is introduced as steam into the middle part of the column.

5. A process as claimed in claim 1, 2, 3 or 4, wherein methyl formate and water are employed in a molar ratio of from 1:2 to 1:10 in hydrolysis (a).

6. In a process for obtaining anhydrous or substantially anhydrous formic acid by hydrolysis of methyl formate, the improvement which comprises:
(a) hydrolyzing methyl formate;
(b) in a first stage distillation column, distilling methanol and excess methyl formate from the hydrolysis mixture obtained in step (a);
(c) extracting the bottom product of the first distillation stage (b), consisting essentially of formic acid and water, by means of a liquid-liquid extraction with an extractant which in the main takes up the formic acid, said extractant being a carboxylic acid amide of the formula

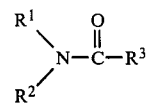

wherein $R^1$ and $R^2$ are akyl, cycloalkyl, aryl or aralkyl or conjointly are 1,4- or 1,5-alkylene, each of 1 to 8 carbon atoms, with the provisio that the sum of the carbon atoms of $R^1$ and $R^2$ is from 7 to 14, and that only one of the radicals is aryl, and where $R^3$ is hydrogen or $C_1$- to $C_4$-alkyl;
(d) in a second stage distillation column, distilling the extract phase, consisting essentially of formic acid, the extractant and a part of the water;
(e) recycling, as vapor, into the lower part of the distillation column of stage (b), the top product obtained from the second distillation stage (d) and consisting essentially of
  (1) all or part of the water introduced into said second stage (d), and
  (2) part of the formic acid;
(f) separating, by distillation in a third stage distillation column, the bottom product of distillation stage (d) consisting essentially of
  (1) the extractant with or without part of the water, and
  (2) the greater part of the formic acid into anhydrous or substantially anhydrous formic acid and the extractant; and
(g) recycling to the process the extractant leaving the third distillation stage (f).

7. A process as claimed in claim 6, wherein the hydrolysis (a) is carried out in the presence of said extractant (I).

8. A process as claimed in claim 6, wherein the distillation steps (b) and (d) are carried out in the single column which performs the functions of the columns of these steps.

9. A process as claimed in claim 6, wherein the water required for the hydrolysis is introduced as steam into the lower part of the column of step (b).

10. A process as claimed in claim 8, wherein the water required for the hydrolysis is introduced as steam into the middle part of the column.

11. A process as claimed in claim 6, 7, 8, 9 or 10, wherein methyl formate and water are employed in a molar ratio of from 1:2 to 1:10 in hydrolysis (a).

12. A process as claimed in claim 8, 9 or 10 wherein the hydrolysis (a) is carried out in the presence of said extractant (I).

* * * * *